United States Patent
Kierkels et al.

(10) Patent No.: US 7,132,466 B2
(45) Date of Patent: Nov. 7, 2006

(54) HALOGEN-FREE FLAME RETARDANT COMPOUNDS

(75) Inventors: Renier Henricus Maria Kierkels, Beegden (NL); Nicolaas Johanna Jozef Aelmans, Da Vlodrop (NL); Patricia Hubertina Cornelis Grolleman, BJ Sittard (NL); Adrianus Wilhelmus Maria Braam, Susteren (NL)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/491,816

(22) PCT Filed: Oct. 1, 2002

(86) PCT No.: PCT/EP02/10994

§ 371 (c)(1),
(2), (4) Date: Aug. 10, 2004

(87) PCT Pub. No.: WO03/031417

PCT Pub. Date: Apr. 17, 2003

(65) Prior Publication Data

US 2004/0259986 A1 Dec. 23, 2004

(30) Foreign Application Priority Data

Oct. 9, 2001  (NL) .................................. 1019144

(51) Int. Cl.
*C08K 5/3492* (2006.01)
(52) U.S. Cl. ...................... 524/100; 524/127; 524/416; 562/18
(58) Field of Classification Search ............... 524/100, 524/127, 416; 562/18
See application file for complete search history.

(56) References Cited

U.S. PATENT DOCUMENTS

| T952,008 I4 | 11/1976 | McCullough et al. ........ 423/305 |
| 4,043,987 A | 8/1977 | Jolicoeur et al. ............ 524/127 |
| 4,396,586 A | 8/1983 | Maurer et al. .............. 423/305 |
| 5,721,281 A * | 2/1998 | Blount ........................ 521/50 |

FOREIGN PATENT DOCUMENTS

| EP | 0049763 | 4/1982 |
| EP | 0614936 | 9/1994 |
| JP | 11-130413 | * 5/1999 |

OTHER PUBLICATIONS

Patent Abstracts of Japan Publication No. 11130413, Publication Date May 18, 1999.

* cited by examiner

*Primary Examiner*—Peter Szekely
(74) *Attorney, Agent, or Firm*—Shiela A. Loggins

(57) ABSTRACT

The invention relates to a compound of the general formula: $Z_1\text{-O-}[m(R_1PO_3),n(R_2HPO_3]Z_2$, represent a copolyphosphate, with m $(R_1PO_3)$ units and n $(R_2HPO_3)$ units; $R_3$ represents an ammonium building block; $R_2$ represents a 1,3,5-triazine building block; $Z_1$ and $Z_2$ represent ammonium or 1,3,5-triazine building blocks, to be chosen independently of each other; m and n represent whole numbers greater than or equal to 1; and m+n numbers greater than 3. The invention further relates to a method for the preparation of the above compound and to flame-retardant polymer compositions in which compounds with the above formula are applied as flame retardant, the use of the halogen-free compound in a coating composition and a substrate containing a coating formed from the coating composition that has been cured.

11 Claims, No Drawings

HALOGEN-FREE FLAME RETARDANT COMPOUNDS

The invention relates to a compound and in particular a halogen-free flame-retardant compound, a method for the preparation thereof, a polymer composition which contains this compound, to the use of said halogen-free compound in a coating composition and a substrate containing a coating formed from the coating composition that has been cured.

Halogen-free flame-retardant compounds are known in the literature. They contain nitrogen or phosphorus compounds or mixtures thereof. Compounds wherein nitrogen and phosphorus are present are also useful, such as melamine-substituted ammonium polyphosphate.

Melamine-substituted ammonium polyphosphate is disclosed in U.S. Pat. No. 4,043,987. As opposed to the statements in this reference, no melamine-substituted ammonium polyphosphate is produced. The reaction product in Example 1 of said publication is wrongly attributed to melamine-substituted ammonium polyphosphate. Although the X-ray diffractogram of ammonium polyphosphate is known since 1965, clarification of the complete X-ray diffractogram of the reaction product formed according to Example 1 of U.S. Pat. No. 4,043,987 was not possible until 1997 when at that time the X-ray diffractogram of urea phosphate had become known. The reaction product from Example 1 now appears to be a mixture of ammonium polyphosphate and urea phosphate. There is no indication that a melamine-substituted ammonium polyphosphate has been formed in reality. Furthermore, the aqueous slurry, made from the reaction product from Example 1 of U.S. Pat. No. 4,043,987, has a pH of 5.68. This indicates that the product contains acid groups. As a result this product is less suitable for use in polymer compositions.

Melamine coated ammonium polyphosphates are disclosed in EP-A-614 936. There is a possibility that ammonium is partially replaced by melamine under the reaction conditions as mentioned in this reference. Presumably acidic groups are to a large extent present in the melamine-coated ammonium polyphosphate. Presumably an insufficient amount of ammonia is present in ammonium polyphosphate, as mentioned in Example 1 of EP-A-614 936.

Flame-retardant compounds containing acid groups, such as the ones according to U.S. Pat. No. 4,043,987, present in polymer compositions have drawbacks. The thermal stability during (melt) processing is inadequate. The consequence is that brittle strands are formed during the compounding process, which break and disturb the compounding process.

The object of the invention is to avoid the above-mentioned disadvantage and to provide an improved flame-retardant compound. This is achieved by means of a compound (I):

in which [m(R$_1$PO$_3$),n(R$_2$HPO$_3$)] represent a copolyphosphate, with m (R$_1$PO$_3$) units and n (R$_2$HPO$_3$) units;
R$_1$ represents an ammonium building block;
R$_2$ represents a 1,3,5-triazine building block;
Z$_1$ and Z$_2$ represent ammonium or 1,3,5-triazine building blocks, to be chosen independently of each other;

m and n represent whole numbers greater than or equal to 1; with the proviso that the sum of m and n is greater than 3.

The compound (I) is characterised by a strong improvement in the thermal stability during the processing of polymers. A further advantage is that during production of a polymer composition with said compound a compact granulate is obtained. The products made of polymers containing the compound (I) exhibit good flame-retardant properties and good mechanical and electrical properties as well as a good colour. The polymer compositions are particularly suitable for technical applications and uses in the electronics or electrical industry.

The water-solubility of a compound (I) is low, which is particularly suitable for application in coating compositions or coatings.

The general terms used throughout the description of this application have the following preferred meanings:

The term copolyphosphate is understood to mean both a random, alternating copolyphosphate and a block copolyphosphate.

An ammonium building block is understood to be an ammonium compound, for example NH$_4$, or an ammonium derivative. A 1,3,5-triazine building block understood to be a melamine or a melamine derivative.

Suitable 1,3,5-triazine building blocks are melamine, ammeline and ammelide, condensation products of melamine such as melam, melem or mixtures thereof.

Preferably melamine, ammelide or ammeline is used as 1,3,5-triazine building block. Melamine is particularly preferred as 1,3,5-triazine building block.

Preferably the copolyphosphate is an alternating copolyphosphate. The mutually alternating triazine and ammonium building blocks can in this way form a 'zip fastener' with a nearby chain of another molecule so that a high thermal stability is achieved.

Preferably the sum of m and n is greater than 20, even more preferably greater than 50. It has been found that compounds (I) wherein the sum of m and n is greater than 50 have a higher thermal stability.

The compounds (I) are not necessarily limited to those of a linear structure. The corresponding branched or cyclic structures are also applicable. Branches or ring structures can be formed via the P or N of the phosphate building block or the 1,3,5-triazine or ammonium building block. Due to the absence of acid groups in the compound (I), the aqueous slurry of this product has a pH of at least 7.

To further improve the compatibility with polymers or optionally to further lower the solubility in water, the compound (I) can be coated. This coating may involve providing the compound (I) with a layer of for example a polymer, including urea-formaldehyde resin, a silicate, zirconate or titanate compound. This coating can be carried out for example by placing the compound (I) in a fluid bed at a higher temperature, for example 120° C., and spraying the compound with, for example, an aqueous solution of a urea-formaldehyde resin. The solution may have a temperature of, for example, 60° C. The urea-formaldehyde resin will thus be deposited on the compound, while the water evaporates from the solution. Generally the quantity of coating will be less than 1 wt. %.

The invention also relates to a method for the preparation of a compound (I).

A method for preparing a substituted ammonium polyphosphate is known from U.S. Pat. No. 4,043,987. In said publication a condensed phosphoric acid and a nitrogen compound are heated above 150° C. It has been demonstrated, however, that in this method no substitution of a 1,3,5-triazine, in this case melamine, on ammonium polyphosphate takes place, but that only a mixture of ammonium polyphosphate and urea phosphate is formed. Moreover, an aqueous slurry made of the reaction product from Example 1 of U.S. Pat. No. 4,043,987 has a pH which is lower than 7. This points to the presence of acid groups in the ammonium polyphosphate.

Another method for preparing substituted polyphosphates, 'amide polyphosphates', is disclosed GB-A-1 440 220. A phosphorus compound and a nitrogen compound are combined with urea and/or urea phosphate and heated to a temperature between 150 and 350° C., optionally in the presence of ammonia. It has been now found that 1,3,5-triazine-substituted ammonium polyphosphates are not prepared under these conditions with said raw materials. Only mixtures of ammonium phosphates and melamine phosphates are formed.

According to the method according to the present invention for the preparation of the compound (I), a starting material that contains a phosphate building block, a 1,3,5-triazine building block and an ammonium building block, which may also contain an—OH group, is heated under a partial ammonia pressure of at least 0.005 MPa at a temperature between 200 and 400° C. Preferably the phosphate building block contains a 1,3,5-triazine building block, an ammonium building block and an—OH group.

During the process a 1,3,5-triazine ammonium polyphosphate is formed, while water is released. At temperatures below 200° C. the process—a polycondensation reaction— is generally too slow, while above 400° C. degradation of the polyphosphate occurs. At the ammonia pressure lower than 0.005 MPa $NH_3$ is split off from the polyphosphate, as a result of which undesirable acid groups are formed.

A phosphate building block comprises any partial structure containing $PO_4^{3-}$ or a derivative thereof, for example a pyrophosphate. Preferably the process temperature lies between 240° C. and 330° C. This gives a practical optimum between reaction rate and the use of elevated temperatures in installations.

Preferably the reaction is carried out at a partial ammonia pressure lower than 5 MPa. Above 5 MPa extremely high requirements are to be met by the construction materials of the installation in which the reaction is carried out. For large-scale operation a partial ammonia pressure range from 0.005 to 0.03 MPa is preferred. The reaction time generally is between 30 min. and 5 h.

In the process according to the invention 1,3,5-triazine-ammonium-phosphate and 1,3,5-triazine-ammonium-pyrophosphate are preferred, in particular the compounds which contain melamine as 1,3,5-triazine, on account of the wide commercial availability of melamine. In this case these are the compounds melamine ammonium phosphate dihydrate and melamine ammonium pyrophosphate.

Also suitable are 1,3,5-triazine building blocks, which have a phosphorus substituent and/or an ammonium building block that has a phosphorus substituent. These substituted building blocks can be present in the simple compound already before the reaction, but can also be formed during the reaction. To be considered in this respect is a 1,3,5-triazine building block and/or ammonium building block of the first main chain, which reacts or is substituted with a phosphorus component of a second main chain.

Optionally it may be decided to add a latent ammonia source, including urea. The water released during the polycondensation reaction then causes urea to decompose into ammonia and carbon dioxide. The quantity of urea to be added preferably is less than 2 moles per mole of the simple compound. This ensures a good balance between the formation of water from the polycondensation reaction and the reaction of this water with urea. Likewise extra urea can be added to bind any water of crystallisation present in the simple compound. Preferably this extra quantity of urea is equimolar to the quantity of water of crystallisation.

The present invention also relates to a polymer composition that shows a good processability, colour and flame-retardant properties. The polymer composition comprises the following components:
35–99 wt. % polymer;
0–80 wt. % reinforcing agents and/or fillers;
1–50 wt. % of a compound (I);
<10 wt. % ammonium polyphosphate (APP);

wherein the weight percentages relate to the total weight of the polymer composition.

Preferably the polymer composition contains less than 5 wt. % APP and in particular less than 2 wt. %, similarly related to the total weight of the polymer composition. In view of the stability during processing a low APP content is important particularly for polymers, which are processed at temperatures above 200° C.

It has been found that flame-retardant polymer compositions according to the present invention exhibit an excellent thermal stability, are excellent flame retardants and give almost no deposits during processing, for example melamine deposits in compounding or injection moulding equipment. The compound (I) has a low sensitivity to hydrolysis and is poorly soluble in water.

The present invention also relates to a polymer composition, wherein the compound (I) is present in a synergistic combination with other flame-retardant components and/or reinforcing agents and/or fillers.

In addition, the usual additives can be present, such as for example heat and UV-stabilisers —including phenolic antioxidants, aromatic amines, phosphates, sulphides, metal salts—particularly copper salts —, UV absorbers, HALS compounds (hindered amine light stabilisers) and metal deactivators; release agents, flow promoting agents, plasticisers, lubricants and/or dispersing agents, including metallic soaps, montanic acid and montanic acid derivatives, fatty acids, fatty acid amides, fatty acid esters, polyethylene waxes—whether or not polar—, paraffin waxes and/or fluoropolymers, nucleating agents and antistatics. Use will generally be made of less than 1 wt. %, relative to the total composition, per additive. This holds insofar as these additives do not have an adverse effect on the properties of the polymer composition.

Polymer compositions which can be made flame-retardant with the compound (I) are preferably based on polymers that require heat-resistant flame retardants such as polyamides, polyimides, polyesters, polystyrenes, polyurethanes, epoxy resins, polycarbonates, polypropylene and mixtures of these materials.

Examples of polyamides are polyamides and co polyamides which have been derived from diamines and dicarboxylic acids and/or from aminocarboxylic acids or the corresponding lactams, such as polyamide 4, polyamide 6, polyamide 11, polyamide 12, polyamide 6/6, 4/6, partially aromatic (co) polyamides, for example polyamides based on an aromatic diamine and adipic acid; polyamides prepared from an alkylene diamine and iso- and/or terephthalic acid and co polyamides thereof.

Examples of polyesters are polyesters derived from dicarboxylic acids and dialcohols and/or from hydroxycarboxylic acids or the corresponding lactones, including polyethylene terephthalate, polypropylene terephthalate, polybutylene terephthalate, poly-1,4-dimethylolcyclohexane terephthalate, polycaprolactone and co polyesters thereof.

Polystyrenes are also understood to be syndiotactic polystyrene and high-impact polystyrene (HIPS). Examples of polyurethanes are polyurethanes derived from diols or polyfunctional polyols and diisocyanates, including 1.6-hexamethylene diisocyanate, methane diphenyl diisocyanate (MDI) and toluene diisocyanate–2.4 and –2.6 (TDI).

Preferably the compound (I) is applied in polymer compositions with polyethylene terephthalate and/or polybutylene terephthalate, with polybutylene terephthalate being given special preference, or with polyamides such as Nylon® 6, 6,6 or 4,6 or with polyurethanes or polyurethane foam.

Examples of coating compositions are pigment-filled alkyd resins, homo- or copolymers based on acrylates, urethanes, esters, epoxies or modifications thereof. Optionally these can be provided with the usual cross linkers. After curing of this coating composition a coating is formed.

The flame-retardant property of the polymer composition can be reinforced by the presence of a compound working synergistically for the compound (I). This generally makes it possible for a lower content of the compound (I) to be chosen. An example of a compound with a synergistic effect is a carbon-forming compound, whether or not in combination with a catalyst promoting the formation of carbon.

As carbon-forming compounds in principle all known substances can be considered that can reinforce the flame-retardant properties of flame-retardant polymer compositions by means of the formation of carbon caused by the fire. The concentration in the total polymer composition of the compound working synergistically for the compound (I) generally is between 0 and 30 wt. %.

Useful as catalyst promoting the formation of carbon are e.g. metal salts of tungstic acid, or a complex acid oxide of tungsten with a metalloid, or salts of tin oxide. Metal salts of tungstic acid are preferably alkali metal salts of tungstic acid and in particular sodium tungstate. A complex acid oxide of tungsten with a metalloid is understood to mean, for example, a silicotungstic acid or phosphotungstic acid.

The quantity of catalyst promoting the formation of carbon that is used in the polymer composition amounts to 0.1–5 wt. %, preferably 0.1–2.5 wt. %.

The flame-retardant properties of the compound (I) according to the invention can be reinforced further when the polymer composition comprises at least one additional flame-retardant component. As additional flame-retarding component in principle all known flame-retardants can be considered. Examples are antimony compounds, such as for example antimony trioxide or sodium antimonate, in combination with halogen compounds; earth alkali metal oxides, for example zinc oxide, magnesium oxide; other metal oxides, for example alumina, silica, iron oxide and manganese oxide; metal hydroxides, for example magnesium hydroxide and aluminium hydroxide; nano-composites; clay such as for example montmorillonite clay and kaolin clay; treated clay such as clay treated with primary ammonium compounds or with quaternary ammonium compounds or with melamine or with phosphorus-containing compounds; silicon-containing compounds such as for example silicates, organosilicon compounds, aromatic organosilicon compounds and silicates, titanates and zirconates; metal borates, for example zinc borate, whether or not hydrated; melamine sulphate; phosphorus-containing compounds such as for example phosphates, phosphate esters, phosphonates, phosphinates, phosphines, phosphine oxides and phosphites; nitrogen-containing compounds such as melamine cyanurate, melamine polyphosphate, higher condensation products of melamine such as melem and melam.

Preferably phosphates, phosphinates and/or phosphonates are used as the phosphorus-containing compound. Even more preferably calcium, zinc or aluminium phosphinates are used.

The content of these phosphorus-containing compounds in the polymer composition may vary between 0 wt. % and 25 wt. %, relative to the weight of the total composition.

Other known compounds present in flame-retardant compositions, such as the anti-drip agent polytetrafluoroethylene, may also be present. The content thereof will be generally lower than 5 wt. %, preferably lower than 1 wt. %, relative to the weight of the total composition.

The content of other flame-retardant components applied in the total polymer composition may vary between broad limits; generally their content lies between 1 and 50 wt. %, relative to the weight of the total composition.

If reinforcing agents and/or fillers are applied in the polymer composition, their content may vary between broad limits and this content is partly determined by the level of (mechanical) properties which one wishes to achieve. Generally the reinforcing agents/fillers content will be not more than 80 wt. % of the total composition. Preferably a reinforced polymer composition will contain 5–50 wt. % reinforcing agents, more preferably 15–45 wt. %. Examples of reinforcing agents are mica, clay, talc, glass fibres, glass beads, glass flakes, aramid fibres and carbon fibres. Reinforcing materials can be applied in the form of fibres, beads, plates, etc. Different reinforcing agents can be combined. However, optical glass fibres are preferred. Fillers are understood to be pigments and/or dyes.

The polymer composition according to the invention can be prepared using the conventional techniques known per se, for example by dry mixing all or a number of components in a tumbler, high-shear mixer, etc., followed by addition of or to the polymer. Liquid resins, for example alkyd resins, can be added directly to the mixer, while solid thermoplastics are melted in a melt mixer, for example a Brabender mixer or a single- or twin-screw extruder or a kneader, after which the flame-retardant and other components can be added. Preferably a twin-screw extruder is used.

The different components of the polymer composition can be metered together to the throat of the extruder. They can be also metered to the extruder at different places. A number of the components that may be present, such as for example dyes, stabilisers, the flame-retardant composition, compounds working synergistically for the compound (I) and/or other flame-retardant components, can be added to the polymer for example in the form of a concentrate, for example in the form of a master batch.

The flame-retardant polymer composition according to the invention can be processed using techniques known to the person skilled in the art, for example injection moulding, into semi-finished products or final products or can be used as coating composition via known application techniques.

The invention also relates to the use of the compound (I) in a coating composition. Such coating compositions can be applied to, inter alia, wood, metal, stone, plastics, fibres and textile, in which case the poor water solubility of the compound (I) is an advantage.

Finally, the invention relates to a substrate containing a coating, formed from a coating composition that has been cured, containing the compound (I).

The substrate is not necessarily limited. All substrates, which are normally provided with a coating, can be considered, such as for example wood, plastic/polymer, metal, glass, etc. The substrate can further have the form of a straight or curved surface or a three-dimensional moulded article. Fibres, (mono) filaments as well as fabrics thereof can be considered.

The invention is further elucidated on the basis of the following examples and comparative experiments:

EXAMPLES

Definition of measurement methods used:
Slurry pH: is measured, at room temperature, after one hour's stirring of slurry with 10 wt. % of the compound according to the invention, in water.
Flame retardation: The flame retardation is measured on test bars, which are subjected to the test method according to Underwriters Laboratories Inc., Bulletin 94, Combustion Test for the Classification of Materials. According to this test method, the materials thus tested are classified as UL94 V0, UL94 V1 or UL94 V2 on the basis of the results obtained. In this context the highest class, V0, represents good flame retardation.
Water solubility: is determined by adding 10 g of the compound to 100 ml water and stirring this for 1 hour, at room temperature
Comparative tracking index (CTI): is measured according to IEC 60112

Comparative Experiment A 47 g Urea is added, with stirring, to 100 g condensed phosphoric acid. Subsequently 8 g melamine is added to the resulting liquid mixture. The mixture is then placed in a furnace at 240° C. for 10 min. The reaction product has a solubility of 5.4 g per 100 ml water. The slurry pH is 5.68.

The product is ground and heated for 13 h in a pressurised reactor at 0.4 MPa and 170° C. The slurry pH of this product is 6.63.

An X-ray diffractogram is recorded using X-ray diffraction. During X-ray diffraction a crystalline substance gives a specific number of reflections to the crystal lattice. This is evident in a diffractogram characterised with a number of lines, the so-called fingerprint. The combination of lines in the diffractogram identifies the substance. Diffractograms of various compounds can be found in several databases. In the clarification of the diffractograms of the present invention use is made of ICDD data (International Centre for Diffraction Data).

The diffractogram of the reaction product formed in Comparative Experiment A is included in Table 1. Table 1 shows that the reaction product consists of a mixture of ammonium poly-phosphate and urea phosphate. Melamine-substituted ammonium polyphosphate is not present.

TABLE 1

| X-ray diffractogram of the reaction product of Comparative Experiment A | | | |
|---|---|---|---|
| Line | d, Å | 2Θ | Line belonging to compound |
| 1 | 6.017 | 14.71 | 1 |
| 2 | 5.705 | 15.52 | 2 |
| 3 | 5.564 | 15.91 | 1 |
| 4 | 5.420 | 16.34 | 1 |
| 5 | 3.808 | 23.34 | 1, 2 |
| 6 | 3.577 | 24.87 | 1, 2 |
| 7 | 3.491 | 25.49 | 1, 2 |
| 8 | 3.412 | 26.09 | 1, 2 |
| 9 | 3.230 | 27.59 | 1, 2 |
| 10 | 3.146 | 28.34 | 2 |
| 11 | 3.093 | 28.84 | 1 |
| 12 | 3.002 | 29.74 | 2 |

TABLE 1-continued

| X-ray diffractogram of the reaction product of Comparative Experiment A | | | |
|---|---|---|---|
| Line | d, Å | 2Θ | Line belonging to compound |
| 13 | 2.925 | 30.54 | 1, 2 |
| 14 | 2.883 | 30.99 | 1, 2 |
| 15 | 2.817 | 31.74 | 1 |
| 16 | 2.747 | 32.57 | 1, 2 |
| 17 | 2.638 | 33.96 | 1, 2 |
| 18 | 2.538 | 35.34 | 1, 2 |
| 19 | 2.416 | 37.19 | 1, 2 |
| 20 | 2.352 | 38.24 | 1, 2 |
| 21 | 2.288 | 39.34 | 1 |

1 = ammonium polyphosphate (form 2)
2 = urea phosphate

Elemental Analysis: C: 4%; N: 18%; P: 29%; H: 4%; O: 45%.

This proves that no melamine-substituted ammonium polyphosphate has been formed in Example 1 of U.S. Pat. No. 4,043,987

Example I 554 g Melamine ammonium phosphate dihydrate ('MAP 2H$_2$O salt') is introduced into a pressurised reactor. The partial ammonia pressure in the pressurised reactor is set at 1.2 MPa; the temperature is set at 315° C. The total reaction time, at a temperature above 200° C., is about 2 h, of which 30 min. at 315° C.

The reaction product is identified with X-ray diffraction, elemental analysis, $^{31}$P-NMR and pH-measurement:
Comparison of the X-ray diffractogram from Table 2a with Table 2b shows that a new compound has been formed;
Nitrogen elemental analysis proves that melamine and ammonium are present in the reaction product;
$^{31}$P-NMR proves that the formed product is a polyphosphate with a degree of polymerisation ('m+n') of 30;
The slurry pH of the formed reaction product is 7.8, which means that no acid groups are present.

The conclusion can be drawn from the above that a new compound is formed, which contains melamine, ammonium and a polyphosphate: a melamine ammonium polyphosphate (a 'MAPP').

The water solubility of the melamine ammonium polyphosphate is 1.1 g per 100 ml water. The X-ray diffractogram of this melamine ammonium polyphosphate is shown in Table 2a. In Table 2b the first 25 lines of melamine ammonium phosphate dihydrate are given.

TABLE 2a

| X-ray diffractogram of the reaction product from Example I | | |
|---|---|---|
| Line | d, Å | I/Io |
| 1 | 8.07 | 12 |
| 2 | 6.85 | 69 |
| 3 | 6.61 | 12 |
| 4 | 5.609 | 100 |
| 5 | 5.311 | 12 |
| 6 | 3.677 | 45 |
| 7 | 3.423 | 72 |
| 8 | 3.255 | 14 |
| 9 | 3.172 | 23 |
| 10 | 3.060 | 12 |
| 11 | 2.814 | 24 |

TABLE 2a-continued

X-ray diffractogram of the reaction product from Example I

| Line | d, Å | I/Io |
|---|---|---|
| 12 | 2.690 | 22 |
| 13 | 2.357 | 12 |

TABLE 2b

First 25 lines of the starting material for the reaction in Example I: melamine ammonium phosphate dihydrate (Source: ICDD 44-1709)

| Line | d (Å) | I/I$_o$ |
|---|---|---|
| 1 | 6.92 | 85 |
| 2 | 6.08 | 15 |
| 3 | 5.94 | 64 |
| 4 | 5.71 | 19 |
| 5 | 5.08 | 15 |
| 6 | 5.01 | 9 |
| 7 | 4.931 | 17 |
| 8 | 4.728 | 20 |
| 9 | 4.600 | 61 |
| 10 | 4.410 | 5 |
| 11 | 4.120 | 4 |
| 12 | 4.028 | 5 |
| 13 | 3.972 | 12 |
| 14 | 3.902 | 15 |
| 15 | 3.651 | 21 |
| 16 | 3.632 | 25 |
| 17 | 3.453 | 68 |
| 18 | 3.303 | 100 |
| 19 | 3.234 | 22 |
| 20 | 3.193 | 18 |
| 21 | 3.140 | 53 |
| 22 | 3.107 | 5 |
| 23 | 3.032 | 11 |
| 24 | 2.997 | 14 |
| 25 | 2.940 | 6 |

Melamine ammonium phosphate is completely converted into a melamine ammonium polyphosphate.

Example II

In a pressurised reactor 1108 g melamine ammonium phosphate dihydrate ('MAP 2H$_2$O salt') is contacted with 600 g urea. The partial ammonia pressure in the reactor initially is 0.05 MPa. The temperature of the pressurised reactor is increased to approximately 315° C. The total reaction time at a temperature above 200° C. is around 2 h, of which 30 min. at 315° C.

The degree of polymerisation ('m+n') of the formed melamine ammonium polyphosphate is determined with $^{31}$P-NMR and is found to be 120. The slurry pH of the formed reaction product is 7.4. The water solubility of the melamine ammonium polyphosphate is 1.0 g per 100 ml water.

Example III

In a pressurised reactor melamine ammonium pyrophosphate is heated stepwise to 315° C. under a partial ammonia pressure of 2 MPa and is subsequently polymerised for 1 hour at 315° C. to form a melamine ammonium polyphosphate. The advantage of stepwise heating is that it prevents deposits of reaction products on the reactor wall—the so-called scaling.

The reaction product is identified with X-ray diffraction, elemental analysis, $^{31}$P-NMR and pH-measurements:

The X-ray diffractogram of Table 3 proves that a new compound has been formed;

Nitrogen elemental analysis proves that melamine and ammonia are present in the reaction product;

$^{31}$P-NMR proves that the formed product is a polyphosphate with a degree of polymerisation ('m+n') of 50;

The slurry pH of the formed reaction product is 7.0, which means that no acid groups are present in the reaction product;

TABLE 3

X-ray diffractogram of the reaction product from Example III

| Line | D (Å) | I/I$_o$ |
|---|---|---|
| 1 | 8.00 | 29 |
| 2 | 6.76 | 53 |
| 3 | 6.53 | 41 |
| 4 | 5.54 | 100 |
| 5 | 5.26 | 33 |
| 6 | 3.725 | 25 |
| 7 | 3.651 | 45 |
| 8 | 3.460 | 28 |
| 9 | 3.395 | 71 |
| 10 | 3.284 | 26 |
| 11 | 3.184 | 64 |

From the above the conclusion can be drawn that a new compound is formed, which contains melamine, ammonium and a polyphosphate (melamine ammonium polyphosphate). In view of the fact that a starting material is used, which differs from the one used in Example I, this copolyphosphate has a different incorporation of ammonium and melamine, resulting in a different crystal lattice. This manifested in a new X-ray diffractogram, other than the diffractogram belonging to the melamine ammonium polyphosphate obtained via experiment 1.

Comparative Experiment B 180.17 g Monoammonium phosphate and 40.14 g of a melamine phosphate compound are introduced into a furnace. While the material is being stirred, the temperature is increased to 190° C. and subsequently stepwise to 260° C. The total reaction time is 3 h. During the synthesis ammonia is released. The reaction product has a lower solubility than APP, 1.7 g in 100 ml water.

The X-ray diffractogram in Table 4 proves that the reaction product consists of a mixture of ammonium polyphosphate and melamine pyrophosphate.

Thermographic analysis, TGA, proves that the thermostability of the reaction mixture is comparable with that of APP. The mass loss starts at around 220° C.

The slurry pH is 5.7, which demonstrates that the reaction mixture contains acid groups.

TABLE 4

X-ray diffractogram of the substance obtained in Comparative Experiment B

| Line | d, Å | Line belonging to compound |
|---|---|---|
| 1 | 10.8 | 3 |
| 2 | 7.38 | 3 |
| 3 | 6.89 | 1 |
| 4 | 6.63 | 1 |
| 5 | 6.03 | 1 |
| 6 | 5.42 | 1 |
| 7 | 4.96 | 3 |
| 8 | 4.75 | 3 |
| 9 | 4.52 | 3 |

TABLE 4-continued

X-ray diffractogram of the substance
obtained in Comparative Experiment B

| Line | d, Å | Line belonging to compound |
|---|---|---|
| 10 | 3.816 | 1 |
| 11 | 3.498 | 1 |

1 = ammonium polyphosphate (form 1)
3 = melamine pyrophosphate

Comparative Experiment C 204.05 g Melamine phosphate and 158.07 g urea phosphate are introduced into a furnace. The temperature is increased to 190° C. and subsequently stepwise to 260° C. while stirring. The total reaction time is 3 h. During the synthesis ammonia is released. The reaction product has lower water solubility than APP, 1.2 g in 100 ml water. The reaction product consists of a mixture of ammonium polyphosphate and melamine pyrophosphate. The X-ray diffractogram is comparable with the diffractogram from Comparative Experiment B. The stability in TGA is likewise comparable with that of the reaction product from Comparative Experiment B.

Comparative Experiment D 31.5 g Melamine and 158.07 g urea phosphate are introduced into a furnace. The temperature is increased to 190° C. and subsequently stepwise to 260° C. while stirring. The total reaction time is 3 h. During the synthesis ammonia is released. The reaction product has lower water solubility than APP: 2.1 g in 100 ml water.

The X-ray diffractogram in Table 5 shows that the reaction product consists of a mixture of ammonium polyphosphate and free melamine;

The stability of the reaction product in TGA is comparable with that of the reaction product from Comparative Experiment B (mass loss starts at 230° C.).

TABLE 5

X-ray diffractogram of the substance
obtained in Comparative Experiment D

| Line | d, Å | Line belonging to compound |
|---|---|---|
| 1 | 11.8 | 4 |
| 2 | 10.8 | 4 |
| 3 | 6.89 | 1 |
| 4 | 6.63 | 1 |
| 5 | 6.03 | 1 |
| 6 | 5.43 | 1 |
| 7 | 4.98 | 4 |
| 8 | 4.08 | 4 |
| 9 | 4.01 | 4 |
| 10 | 3.816 | 1 |
| 11 | 3.498 | 1 |

1 = ammonium polyphosphate, (form 2)
4 = melamine

Comparative Experiment E 204 g Melamine phosphate, 230 g monoammonium phosphate and 60 g urea are introduced into a closed furnace. The temperature is subsequently increased stepwise to approximately 310° C. The total reaction time is 4 h. The reaction product has lower solubility than APP: 1.8 g in 100 ml water.

The thermostability measured with TGA is comparable with that of APP (mass loss starts at approximately 220° C.).

The X-ray diffractogram in Table 6 proves that a mixture of ammonium polyphosphate and melamine polyphosphate has been formed;

TABLE 6

X-ray diffractogram of the substance
obtained in Comparative Experiment E

| Line | d, Å | Line belonging to compound |
|---|---|---|
| 1 | 10.7 | 5 |
| 2 | 8.01 | 5 |
| 3 | 6.89 | 1 |
| 4 | 6.63 | 1 |
| 5 | 6.03 | 1 |
| 6 | 5.44 | 1 |
| 7 | 4.86 | 5 |
| 8 | 4.16 | 5 |
| 9 | 3.979 | 5 |
| 10 | 3.816 | 1 |
| 11 | 3.498 | 1 |

1 = ammonium polyphosphate (form 2)
5 = melamine polyphosphate

Comparative Experiment F 31.5 g Melamine, 230 g monoammonium phosphate and 60 g urea are introduced into a closed furnace. The temperature is subsequently increased stepwise to approximately 310° C. The total reaction time is 4 h.

The reaction product has a lower solubility than APP: 2.5 g in 100 ml water. The thermostability measured with TGA is comparable with that of APP (mass loss starts at approximately 220° C.). The X-ray diffractogram in Table 7 shows that mainly ammonium polyphosphate and free melamine are present in the reaction product.

TABLE 7

X-ray diffractogram of the substance
in Comparative Experiment F

| Line | D, Å | Line belonging to compound |
|---|---|---|
| 1 | 10.8 | 4 |
| 2 | 6.02 | 6 |
| 3 | 5.42 | 6 |
| 4 | 5.02 | 4 |
| 5 | 4.09 | 4 |
| 6 | 5.45 | 6 |
| 7 | 4.00 | 4 |
| 8 | 3.812 | 5 |
| 9 | 3.495 | 6 |
| 10 | 3.407 | 6 |

4 = melamine
5 = melamine polyphosphate
6 = ammonium polyphosphate ('form 1')

Example IV

Starting from the melamine ammonium polyphosphate from Example I a polymer composition containing polyamide, a so-called polyamide compound, is prepared. The following materials are added to a Werner & Pfleiderer ZSK30/33D twin-screw extruder:

| | |
|---|---|
| Polyamide 6 (Akulon ® K123 - DSM) | 35.0 wt. % |
| Compound from Example I | 35.0 wt. % |
| Glass fibres (OCF 173 X10C) | 30.0 wt. % |

The extruder is provided with vacuum degassing. The degassing is set at a vacuum of 0.08 MPa. The polymer strands obtained are passed through a cooling tank with water and subsequently chopped into granulate. The granulate is compact and has a light cream colour Using a Battenfeld injection moulding machine type BA350 CDplus test bars with a thickness of 1.6 mm are manufactured according to Underwriter's Laboratories UL94. The melt temperature is set at 275° C., the mould temperature is 85° C. Injection moulding took place without problems, the products has a good mould release behaviour and no material is deposited in the mould. The product has a creamish colour.

The flame retardation of the test bars is determined according to Underwriter's Laboratories UL94. The test bars achieved good flame retardation, classified as V0 according to UL94.

As electrical property the CTI, the comparative tracking index, is measured. The value found is 350 Volt.

Comparative Experiment G

Starting from the product from Comparative Experiment A the polyamide compound is prepared. The following materials are added to a Werner & Pfleiderer ZSK30/33D twin-screw extruder:

| | |
|---|---|
| Polyamide 6 (Akulon ® K123 - DSM) | 35.0 wt. % |
| Compound from Comparative Experiment A | 35.0 wt. % |
| Glass fibres (OCF 173 X10C) | 30.0 wt. % |

The extruder is provided with vacuum degassing. The degassing is set at a vacuum of 0.08 MPa. Upon degassing ammonia is detected by means of Dräger® tubes. The quantity of ammonia released is higher by a factor of 5 than in Example IV.

The polymer strands, which exited from the head of the extruder, are swollen and regularly exhibited strand breakage, so that the compounding process has to be interrupted. The strands are led through a cooling tank with water and subsequently chopped into granulate. While the strands are being led through the water in the cooling tank, the water showed a bluish discoloration and a soap-like layer is formed on the water surface. In addition, strong discoloration of the polymer strand and thus of the granulate occurred.

By means of a Battenfeld injection moulding machine type BA350 CDplus test bars with a thickness of 1.6 mm are manufactured according to Underwriter's Laboratories UL94. The melt temperature is set at 275° C., the mould temperature is 85° C. During injection moulding the following problems occurred: the products adhered in the mould and as a result are poorly released from the mould. In the products cavities resulting from gas bubbles are observed.

The flame retardation of the test bars is determined according to Underwriter's Laboratories UL94. The test bars achieved a flame retardation classified as V0 according to UL94. The CTI is less than 175 Volt.

Comparative Experiment H

Starting from the product from Comparative Experiment D a polyamide compound is prepared. The following materials are added to a Werner & Pfleiderer ZSK30/33D twin-screw extruder:

| | |
|---|---|
| Polyamide 6 (Akulon ® K123-DSM) | 35.0 wt. % |
| Compound from Comparative Experiment A | 35.0 wt. % |
| Glass fibres (OCF 173 X10C) | 30.0 wt. % |

The extruder is provided with vacuum degassing. The degassing is set at a vacuum of 0.08 MPa. Upon degassing ammonia is observed.

The degassing is blocked within half an hour as a result of sublimated melamine and therefore has to be regularly cleaned. At the head of the extruder, where the polymer strands exited before reaching the cooling tank, a white vapour is observed. This vapour turned out to be sublimating melamine.

The polymer strands obtained, which have a swollen appearance, are led through a cooling tank with water and are subsequently chopped into granulate. Strand breakage occurred regularly. While the strands are being led through the water in the cooling tank, the water showed a bluish discoloration and a deposit is observed on the surface of the cooling water. In addition, strong discoloration of the strand and thus of the granulate took place.

By means of a Battenfeld injection moulding machine type BA350 CDplus test bars with a thickness of 1.6 mm are manufactured according to Underwriter's Laboratories UL94. The melt temperature is set at 275° C., the mould temperature is 85° C. During injection moulding the products adhered in the mould, mould release is poor. Furthermore a deposit is formed in the mould so that the mould has to be regularly cleaned. The test bars displayed discolorations and stains.

The flame retardation of the test specimens is determined according to Underwriter's Laboratories UL94. The test specimens achieved a V0 classification.

The invention claimed is:

1. A compound of the formula

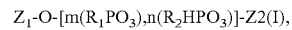

$Z_1$-O-[m($R_1PO_3$),n($R_2HPO_3$)]-$Z_2$(I), wherein

[m($R_1PO_3$),n($R_2HPO_3$)] represent a copolyphosphate, with m ($R_1PO_3$) units and n ($R_2HPO3$) units;

$R_1$ is an ammonium building block;

$R_2$ is a 1,3,5-triazine building block;

$Z_1$ and $Z_2$ are ammonium or 1,3,5-triazine building blocks, to be chosen independently of each other;

m and n are whole numbers greater than or equal to 1; with the proviso that the sum of m and n is greater than 3;

obtained by heating a simple compound containing a phosphate building block, a 1,3,5-tirazine building block and an ammonium building block under a partial ammonia pressure of at least 0.005 MPa at a temperature between 200 and 400° C.

2. A compound obtained according to claim 1, wherein the copolyphosphate consists of an alternating copolyphosphate.

3. A compound obtained according to claim 1, in which the sum of m and n is greater than 20.

4. A compound obtained according to claim 1, in which melamine, ammeline, ammelide or condensation products of melamine including melam, melem or mixtures thereof are used as the triazine building block.

5. A polymer composition, wherein the compound (I) obtained according to claim 1 is present in a synergistic combination with other flame-retardant components and/or reinforcing agents and/or fillers.

6. A polymer composition comprising:
- 35–99 wt. % polymer;
- 0–80 wt. % reinforcing agents and/or fillers;
- 1–50 wt. % compound (I) obtained according to claim 1; and
- <10 wt. % ammonium polyphosphate.

7. A polymer composition according to claim 6, wherein less than 5 wt. % ammonium polyphosphate, relative to the total weight of the polymer composition, is present.

8. A polymer composition according to claim 7, wherein less than 2 wt. % ammonium polyphosphate, relative to the total weight of the polymer composition, is present.

9. A substrate comprising a coating, formed from a coating composition that has been cured, containing the compound (I) obtained according to claim 1.

10. A coating composition comprising the compound (I) obtained according to claim 1.

11. A method of flame-retarding a polymer by incorporating the compound (I) obtained according to claim 1 into the polymer.

* * * * *